United States Patent [19]
Seitz et al.

[11] Patent Number: 6,130,251
[45] Date of Patent: *Oct. 10, 2000

[54] ALKOXIMINOACETIC ACID AMIDES

[75] Inventors: Thomas Seitz, Langenfeld; Gerd Hänssler, Leverkusen; Klaus Stenzel, Düsseldorf, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/875,300

[22] PCT Filed: Jan. 17, 1996

[86] PCT No.: PCT/EP96/00179

§ 371 Date: Jul. 23, 1997

§ 102(e) Date: Jul. 23, 1997

[87] PCT Pub. No.: WO96/23763

PCT Pub. Date: Aug. 8, 1996

[30] Foreign Application Priority Data

Jan. 30, 1995 [DE] Germany .......................... 195 02 813
Feb. 1, 1995 [DE] Germany .......................... 195 03 162
Mar. 24, 1995 [DE] Germany .......................... 195 10 770
Jul. 25, 1995 [DE] Germany .......................... 195 27 099
Nov. 20, 1995 [DE] Germany .......................... 195 43 199

[51] Int. Cl.⁷ .......................... A01N 37/18; C07C 233/05
[52] U.S. Cl. .......................... 514/620; 514/456; 514/464; 514/519; 514/520; 514/599; 514/619; 549/366; 549/441; 558/389; 558/414; 564/74; 564/133; 564/134; 564/164; 564/165

[58] Field of Search ...................... 514/619, 620, 514/599, 456, 464, 519, 520; 564/133, 134, 164, 74, 165; 549/366, 441; 558/389, 414

[56] References Cited

U.S. PATENT DOCUMENTS 5,057,537 10/1991 Wenderoth et al. .
5,206,266 4/1993 Schuetz et al. .

FOREIGN PATENT DOCUMENTS 602514 6/1994 European Pat. Off. .
2-200658 8/1990 Japan .
WO 94 26700 11/1994 WIPO .

OTHER PUBLICATIONS

Abstract of Japanese Patent No. 02 200 658 published Aug. 8, 1990.

Abstract of Hungarian Patent T/53776, Dec. 28, 1990.

Abstract of Hungarian Patent T/53777, Dec. 28, 1990.

*Primary Examiner*—Shailendra Kumar
*Attorney, Agent, or Firm*—Norris, McLaughlin & Marcus, P.A.

[57] ABSTRACT

The invention relates to new alkoximinoacetic acid amides, a process for their preparation and their use as agents for combating pests.

8 Claims, No Drawings

ALKOXIMINOACETIC ACID AMIDES

This application is a 371 of PCT/EP96/00179, filed Jan. 17, 1996.

The invention relates to new alkoximinoacetic acid amides, a process for their preparation and their use as agents for combating pests.

New compounds of the general formula (I)

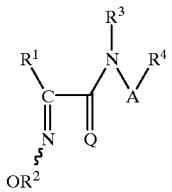

in which
A represents a single bond or optionally substituted alkylene,
Q represents oxygen or sulphur,
$R^1$ represents in each case optionally substituted cycloalkyl, cycloalkenyl, aryl or heterocyclyl,
$R^2$ and $R^3$ are identical or different and in each case represent hydrogen or in each case optionally substituted alkyl, alkenyl, alkinyl or cycloalkyl, and
$R^4$ represents in each case optionally substituted cycloalkyl, cycloalkenyl, aryl or heterocyclyl,
have been found.

In the definitions, the saturated or unsaturated hydrocarbon chains, such as alkyl, alkanediyl, alkenyl or alkinyl, including when linked with heteroatoms, such as in alkoxy, alkylthio or alkylamino, are in each case straight-chain or branched.

Halogen in general represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl or phenanthryl, preferably phenyl or naphthyl, in particular phenyl.

Heterocyclyl represents saturated or unsaturated and aromatic, cyclic compounds in which at least one ring member is a heteroatom, i.e. an atom which differs from carbon. If the ring contains several heteroatoms, these can be identical or different. Heteroatoms are preferably oxygen, nitrogen or sulphur.

Cyclic compounds optionally form a polycyclic ring system together with further carbocyclic or heterocyclic fused-on or bridged rings. Mono- or bicyclic ring systems, in particular mono- or bicyclic aromatic ring systems, are preferred.

Cycloalkyl represents saturated carbocyclic, cyclic compounds which optionally form a polycyclic ring system with further carbocyclic, fused-on or bridged rings. Cycloalkenyl represents carbocyclic, cyclic compounds which contain at least one double bond and optionally form a polycyclic ring system with further carbocyclic, fused-on or bridged rings.

Finally, it has been found that the new alkoximinoacetic acid amides of the general formula (I) have a very potent fungicidal action.

Where appropriate, the compounds according to the invention are in the form of mixtures of various possible isomeric forms, in particular stereoisomers, such as, for example, E and Z, threo and erythro and optical isomers. Both the E and the Z isomers and also the threo and erythro isomers as well as the optical isomers and any desired mixtures of these isomers are described and claimed.

The invention preferably relates to compounds of the formula (I) in which
A represents a single bond, or represents alkylene having 1 to 6 carbon atoms which is optionally mono- or polysubstituted by identical or different substituents, the possible substituents preferably being chosen from the following list:
  halogen, cyano, nitro, amino, hydroxyl, formyl, carboxyl, carbamoyl or thiocarbamoyl;
  in each case straight-chain or branched alkoxy, alkylthio, alkylsulphinyl or alkylsulphonyl having in each case 1 to 6 carbon atoms;
  in each case straight-chain or branched alkenyl or alkenyloxy having in each case 2 to 6 carbon atoms;
  in each case straight-chain or branched halogenoalkoxy, halogenoalkylthio, halogenoalkylsulphinyl or halogenoalkylsulphonyl having in each case 1 to 6 carbon atoms and 1 to 13 identical or different halogen atoms;
  in each case straight-chain or branched halogenoalkenyl or halogenoalkenyloxy having in each case 2 to 6 carbon atoms and 1 to 13 identical or different halogen atoms;
  in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl parts;
  cycloalkyl having 3 to 6 carbon atoms;
  and substituted aryl or heterocyclyl, in each case optionally mono- or poly-substituted in an identical or different manner by
  halogen, cyano and/or straight-chain or branched alkyl having 1 to 4 carbon atoms
  and/or straight-chain or branched halogenoalkyl having 1 to 4 carbon atoms and 1 to 9 identical or different halogen atoms
  and/or straight-chain or branched alkoxy or alkylthio having 1 to 4 carbon atoms
  and/or straight-chain or branched halogenoalkoxy or halogenoalkylthio having 1 to 4 carbon atoms and 1 to 9 identical or different halogen atoms
  and/or in each case divalent alkylene or dioxyalkylene having in each case I to 6 carbon atoms and optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms,
Q represents oxygen or sulphur,
$R^1$ represents aryl, cycloalkyl or cycloalkenyl having 3 to 7 carbon atoms or heterocyclyl having 3 to 12 ring members, in each case optionally mono- or polysubstituted by identical or different substituents, the possible substituents preferably being chosen from the following list:
  halogen, cyano, nitro, amino, hydroxyl, formyl, carboxyl, carbamoyl or thiocarbamoyl;
  in each case straight-chain or branched alkyl, alkoxy, alkylthio, alkylsulphinyl or alkylsulphonyl having in each case 1 to 8 carbon atoms;
  in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 8 carbon atoms in the individual alkyl parts;

in each case divalent alkylene or dioxyalkylene having in each case 1 to 6 carbon atoms and in each case optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and substituted aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, in each case optionally mono- or polysubstituted in an identical or different manner by halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or in each case divalent alkylene or dioxyalkylene having in each case 1 to 6 carbon atoms and optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydrogen, or represents alkyl having 1 to 4 carbon atoms, alkenyl or alkinyl having in each case 2 to 4 carbon atoms or cycloalkyl having 3 to 6 carbon atoms, in each case optionally mono- or polysubstituted in an identical or different manner by halogen, cyano, hydroxyl, amino, $Cl-C_4$-alkoxy, $C_1-C_4$-alkylthio, $C_1-C_4$-alkylsulphinyl or $C_1-C_4$-alkylsulphonyl (which can in each case be optionally substituted by halogen) or by optionally substituted phenyl, $R^3$ represents hydrogen or alkyl having 1 to 4 carbon atoms, $R^4$ represents aryl, cycloalkyl or cycloalkenyl having 3 to 8 carbon atoms or heterocyclyl having 3 to 12 ring members, in each case optionally mono- or polysubstituted by identical or different substituents, the possible substituents preferably being chosen from the following list:

halogen, cyano, nitro, amino, hydroxyl, formyl, carboxyl, carbamoyl or thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl parts;

in each case divalent alkylene or dioxyalkylene having in each case 1 to 6 carbon atoms and in each case optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and substituted aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, in each case optionally mono- or polysubstituted in an identical or different manner by halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or in each case divalent alkylene or dioxyalkylene having in each case 1 to 6 carbon atoms and optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms.

The invention particularly relates to compounds of the formula (I) in which

A represents a single bond, or represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methylpropylene) which are optionally mono- or polysubstituted in an identical or different manner by fluorine, chlorine, cyano or methoxy, Q represents oxygen or sulphur, $R^1$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, in each case optionally mono- to trisubstituted, the possible substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl;

cyclopropyl, cyclobutyl, cyclopentyl or cyclohexyl;

phenyl, benzyl, phenoxy and benzyloxy which are optionally substituted by the abovementioned substituents, $R^2$ represents hydrogen, or represents methyl, ethyl, n- or i-propyl or n-, i-, s-or t-butyl, or represents benzyl or propargyl or allyl, $R^3$ represents hydrogen, or represents methyl or ethyl, $R^4$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, in each case optionally mono- to trisubstituted, the possible substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl;

cyclopropyl, cyclobutyl, cyclopentyl or cyclohexyl.

Particularly preferred compounds of the formula (I) are those in which

A represents a single bond, or represents methylene, 1,1-ethylene, 1,2-ethylene, 1,1-, 1,2-, 1,3- or 2,2-propylene, 1,1-, 1,2-, 1,3-, 1,4-, 2,2-, 2,3-butylene or 1,1-, 1,2- or 1,3-(2-methylpropylene), which are optionally mono- or polysubstituted in an identical or different manner by fluorine, chlorine, cyano or methoxy, Q represents oxygen or sulphur, $R^1$ represents cyclobutyl, cyclopentyl or cyclohexyl, in each case optionally mono- to hexasubstituted, preferred substituents being those mentioned below;

or represents phenyl, naphthyl, furyl, benzofuranyl, thienyl, benzothienyl, pyridyl, quinolyl, tetrahydrofuryl or perhydropyranyl, in each case optionally mono- to trisubstituted, the possible substituents preferably being chosen from the following list:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

in each case. divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl;

cyclopropyl, cyclopentyl or cyclohexyl;

phenyl, phenoxy or benzyloxy optionally substituted by the abovementioned substituents;

$R^2$ represents hydrogen, methyl, ethyl, n- or i-propyl or n-, i- or t-butyl, or represents benzyl or allyl, $R^3$ represents hydrogen or methyl, $R^4$ represents cyclopropyl, cyclobutyl, cyclopentyl or cyclohexyl, in each case optionally mono- to hexasubstituted, preferred substituents being those mentioned below;

or represent phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, in each case optionally mono- to trisubstituted, the possible substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methyl sulphonyloxy, ethyl sulphonyloxy, hydroximinomethyl, hydroximinoethyl, methoximinomethyl, ethoximinomethyl, methoximinoethyl or ethoximinoethyl;

in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl, cyclopropyl, cyclobutyl, cyclopentyl or cyclohexyl.

An especially preferred group of compounds according to the invention are those compounds of the formula (I) in which A represents a single bond, or represents methylene, 1,1-ethylene, 1,2-ethylene, 1,1-propylene, 1,2-propylene, 1,3-propylene or 2,2-propylene, Q represents oxygen, $R^1$ represents phenyl, thienyl or furanyl, which are optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio, or represents phenyl which is substituted by in each case optionally fluorine-substituted 3,4-methyleneand ethylenedioxo, propane-1,3-diyl or butane-1,4-diyl, or represents naphthyl, benzofuranyl or benzothienyl, $R^2$ represents hydrogen, methyl or ethyl, or represents n- or i-propyl, or represents n-, i-, s- or t-butyl, or represents benzyl or allyl, $R^3$ represents hydrogen or methyl, $R^4$ represents cyclohexyl or optionally mono- to trisubstituted phenyl, thienyl, furyl, benzofuryl, benzothienyl, pyridyl, pyrimidinyl, naphthyl or quinolyl, the possible substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluoro-chloromethylthio, trifluoromethylthio, trifluoromethylsulphinyl or trifluoromethylsulphonyl, methylamino, ethylamino, n- or i-propylarnino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl.

Compounds of the formula (I) which are of special interest are those in which the radical $R^1$ represents phenyl which is unsubstituted or substituted in the 3- and/or 4-position, or furanyl or thienyl, which are unsubstituted or substituted in the 4-and/or 5-position, the substituents chosen being those mentioned above, and in particular chlorine, bromine, fluorine, nitro, methylsulphonyl, phenyl, phenoxy, benzyloxy, cyclopropyl, cyclohexyl, methyl, ethyl, n- and i-propyl, n-, i-, s- and t-butyl, n-pentyl, n-hexyl, n-heptyl, methoxy, ethoxy, methylthio, trifluoromethyl and trifluoromethoxy, or phenyl substituted by in each case optionally fluorine-substituted 3,4-methylene- and ethylenedioxo, propane-1,3-diyl and butane-1,4-diyl, or naphthyl, benzofuranyl or benzothienyl which are substituted in the 2-position.

Compounds of the formula (I) which are also particularly preferred are those in which $R^2$ represents methyl or ethyl.

Compounds of the formula (I) which are also particularly preferred are those in which $R^3$ represents hydrogen.

Compounds of the formula (I) which are also particularly preferred are those in which $R^4$ represents phenyl which is substituted by methoxy in the 3- and 4-position.

The abovementioned definitions of radicals given generally or in preferred ranges apply both to the end products of the formula (I) and correspondingly to the starting substances or intermediate products required in each case for the preparation.

These definitions of radicals can be combined with one another as desired, that is to say also between the stated ranges of preferred compounds.

Preferred individual compounds can be seen from the following tables:

TABLE 1

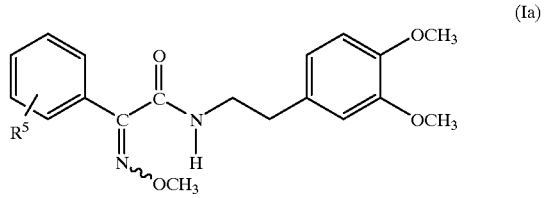

(Ia)

| Compound No. | $R^5$ |
|---|---|
| Ia-1 | Hydrogen |
| Ia-2 | 4-Chloro |
| Ia-3 | 4-Fluoro |
| Ia-4 | 4-Bromo |
| Ia-5 | 4-Methyl |
| Ia-6 | 4-Ethyl |
| Ia-7 | 4-iso-Propyl |
| Ia-8 | 4-n-Propyl |
| Ia-9 | 4-n-Butyl |
| Ia-10 | 4-iso-Butyl |
| Ia-11 | 4-tert.-Butyl |
| Ia-12 | 4-sec.-Butyl |
| Ia-13 | 4-Methoxy |
| Ia-14 | 4-Ethoxy |
| Ia-15 | 4-Methylthio |
| Ia-16 | 4-Trifluoromethyl |
| Ia-17 | 3-Chloro |
| Ia-18 | 3-Fluoro |
| Ia-19 | 3-Bromo |
| Ia-20 | 3-Methyl |

TABLE 1-continued (Ia)

| Compound No. | R⁵ |
|---|---|
| Ia-21 | 3-Ethyl |
| Ia-22 | 3-iso-Propyl |
| Ia-23 | 3-n-Propyl |
| Ia-24 | 3-n-Butyl |
| Ia-25 | 3-iso-Butyl |
| Ia-26 | 3-tert.-Butyl |
| Ia-27 | 3-sec.-Butyl |
| Ia-28 | 3-Methoxy |
| Ia-29 | 3-Ethoxy |
| Ia-30 | 3-Methylthio |
| Ia-31 | 3-Trifluoromethyl |
| Ia-32 | 3,4-Dichloro |
| Ia-33 | 3,4-Difluoro |
| Ia-34 | 3,4-Dibromo |
| Ia-35 | 3,4-Dimethyl |
| Ia-36 | 3,4-Diethyl |
| Ia-37 | 3,4-OCH$_2$O |
| Ia-38 | 3,4-OCH$_2$CH$_2$O |
| Ia-39 | 3,4-OCF$_2$O |
| Ia-40 | 3,4-OCF$_2$CF$_2$O |
| Ia-41 | 3,4-(CH$_2$)$_3$ |
| Ia-42 | 3,4-(CH$_2$)$_4$ |
| Ia-43 | 3,4-Di-methoxy |
| Ia-44 | 3,4-Diethoxy |
| Ia-45 | 3,4-Dimethylthio |
| Ia-46 | 3,4-Di-trifluoromethyl |
| Ia-47 | 3-Chloro, 4-Methyl |
| Ia-48 | 4-Chloro, 3-Methyl |
| Ia-49 | 3-Chloro, 4-Methoxy |
| Ia-50 | 4-Chloro, 3-Methoxy |
| Ia-51 | 3-Chloro, 4-Ethyl |
| Ia-52 | 4-Chloro, 3-Ethyl |
| Ia-53 | 3-Methoxy, 4-Ethoxy |
| Ia-54 | 4-Methoxy, 3-Ethoxy |
| Ia-55 | 3-Methyl, 4-Methoxy |
| Ia-56 | 4-Methyl, 3-Methoxy |
| Ia-57 | 3-Methyl, 4-Ethyl |
| Ia-58 | 4-Methyl, 3-Ethyl |
| Ia-59 | 3-Methoxy, 4-Ethyl |
| Ia-60 | 4-Methoxy, 3-Ethyl |
| Ia-61 | 4-Nitro |
| Ia-62 | 4-Methylsulfonyl |
| Ia-63 | 4-Phenoxy |
| Ia-64 | 4-Phenyl |
| Ia-65 | 4-Benzyloxy |
| Ia-66 | 4-Pentyl |
| Ia-67 | 4-Hexyl |
| Ia-68 | 4-Heptyl |
| Ia-69 | 4-Cyclopropyl |
| Ia-70 | 4-Cyclohexyl |

TABLE 2

(Ib)

| Compound No. | R⁵ |
|---|---|
| Ib-1 | Hydrogen |
| Ib-2 | 4-Chloro |
| Ib-3 | 4-Fluoro |
| Ib-4 | 4-Bromo |
| Ib-5 | 4-Methyl |
| Ib-6 | 4-Ethyl |
| Ib-7 | 4-iso-Propyl |
| Ib-8 | 4-n-Propyl |
| Ib-9 | 4-n-Butyl |
| Ib-10 | 4-iso-Butyl |
| Ib-11 | 4-tert.-Butyl |
| Ib-12 | 4-sec.-Butyl |
| Ib-13 | 4-Methoxy |
| Ib-14 | 4-Ethoxy |
| Ib-15 | 4-Methylthio |
| Ib-16 | 4-Trifluoromethyl |
| Ib-17 | 5-Chloro |
| Ib-18 | 5-Fluoro |
| Ib-19 | 5-Bromo |
| Ib-20 | 5-Methyl |
| Ib-21 | 5-Ethyl |
| Ib-22 | 5-iso-Propyl |
| Ib-23 | 5-n-Propyl |
| Ib-24 | 5-n-Butyl |
| Ib-25 | 5-iso-Butyl |
| Ib-26 | 5-sec.-Butyl |
| Ib-27 | 5-tert.-Butyl |
| Ib-28 | 5-Methoxy |
| Ib-29 | 5-Ethoxy |
| Ib-30 | 5-Methylthio |
| Ib-31 | 5-Trifluoromethyl |
| Ib-32 | 4,5-Dichlor |
| Ib-33 | 4,5-Difluor |
| Ib-34 | 4,5-Dibrom |
| Ib-35 | 4,5-Dimethyl |
| Ib-36 | 4,5-Diethyl |
| Ib-37 | 4,5-Di-methoxy |
| Ib-38 | 4,5-Di-trifluoromethyl |
| Ib-39 | 4-Chloro, 5-Methyl |
| Ib-40 | 5-Chloro, 4-Methyl |

TABLE 3

(Ic)

| Compound No. | R⁵ |
|---|---|
| Ic-1 | Hydrogen |
| Ic-2 | 4-Chloro |
| Ic-3 | 4-Fluoro |
| Ic-4 | 4-Bromo |
| Ic-5 | 4-Methyl |
| Ic-6 | 4-Ethyl |
| Ic-7 | 4-iso-Propyl |
| Ic-8 | 4-n-Propyl |

TABLE 3-continued

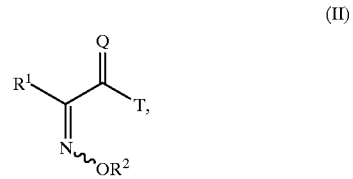

(Ic)

| Compound No. | $R^5$ |
|---|---|
| Ic-9 | 4-n-Butyl |
| Ic-10 | 4-iso-Butyl |
| Ic-11 | 4-tert.-Butyl |
| Ic-12 | 4-sec.-Butyl |
| Ic-13 | 4-Methoxy |
| Ic-14 | 4-Ethoxy |
| Ic-15 | 4-Methylthio |
| Ic-16 | 4-Trifluoromethyl |
| Ic-17 | 5-Chloro |
| Ic-18 | 5-Fluoro |
| Ic-19 | 5-Bromo |
| Ic-20 | 5-Methyl |
| Ic-21 | 5-Ethyl |
| Ic-22 | 5-iso-Propyl |
| Ic-23 | 5-n-Propyl |
| Ic-24 | 5-n-Butyl |
| Ic-25 | 5-iso-Butyl |
| Ic-26 | 5-sec.-Butyl |
| Ic-27 | 5-tert.-Butyl |
| Ic-28 | 5-Methoxy |
| Ic-29 | 5-Ethoxy |
| Ic-30 | 5-Methylthio |
| Ic-31 | 5-Trifluoromethyl |
| Ic-32 | 4,5-Dichloro |
| Ic-33 | 4,5-Difluoro |
| Ic-34 | 4,5-Dibromo |
| Ic-35 | 4,5-Dimethyl |
| Ic-36 | 4,5-Diethyl |
| Ic-37 | 4,5-Di-methoxy |
| Ic-38 | 4,5-Di-trifluoromethyl |
| Ic-39 | 4-Chloro, 5-Methyl |
| Ic-40 | 5-Chloro, 4-Methyl |

TABLE 4

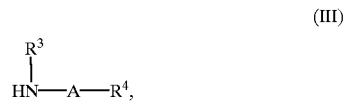

(Id)

| Compound No | $R^1$ |
|---|---|
| Id-1 | 2-Naphthyl |
| Id-2 | 2-Benzofuranyl |
| Id-3 | 2-Benzothienyl |

Table 5

Compounds Ia-1 to Id-3 corresponding to the formulae Ia, Ib, Ic and Id, wherein the 3,4-dimethoxyphenyl group (in general designated $R^4$) is replaced by a phenyl radical which carries the substituents stated in each case as $R^5$ in the compounds Ia-1 to Ia-70.

Table 6

Compounds Ia-1 to Id-3 corresponding to the formulae Ia, Ib, Ic and Id, wherein the 3,4-dimethoxyphenyl group (in general designated $R^4$) is replaced by one of the following trisubstituted phenyl radicals: Substituents: 3,4,5-trimethoxy; 3,4,5-trichloro; 3,4,5-trimethyl.

Table 7

Compounds Ia-1 to Id-3 corresponding to the formulae Ia, Ib, Ic and Id, wherein the methoximino group (in general designated $R^2$) is replaced by an ethoximino group which carries the substituents stated in each case as $R^5$ in the compounds Ia-1 to Ia-70.

It has furthermore been found that the new alkoximinoacetic acid amides of the general formula (I) are obtained by a procedure in which carboxylic acid derivatives of the general formula (II)

$$R^1 \underset{N\sim OR^2}{\overset{Q}{\underset{\|}{C}}} T, \qquad (II)$$

in which

R$^1$, R$^2$ and Q have the abovementioned meaning and
T represents hydroxyl, halogen or alkoxy, are reacted with an amine of the general formula (III)

$$HN\underset{|}{\overset{R^3}{\phantom{N}}}\!\!-\!\!A\!\!-\!\!R^4, \qquad (III)$$

in which

R$^3$, R$^4$ and A have the abovementioned meaning or with a hydrogen halide thereof if appropriate in the presence of an acid acceptor, if appropriate in the presence of a condensing agent and if appropriate in the presence of a diluent.

Formula (II) provides a general definition of the carboxylic acid derivatives required as starting substances for carrying out the process according to the invention. In this formula (II), (Q, R$^1$ and R$^2$) preferably or in particular have those meanings which have already been mentioned as preferred or as particularly preferred for (Q, R$^1$ and R$^2$) in connection with the description of the compounds of the formula (I) according to the invention; T preferably represents alkoxy having 1 to 4 carbon atoms, in particular methoxy or ethoxy, or represents hydroxyl or chlorine.

The starting substances of the formula (II) are known and/or can be prepared by known processes (cf. EP-A 178 826, EP-A 242 081, EP-A 382 375, EP-A 493 711, EP-A 432 503, DE-A 3 938 054).

Formula (III) provides a general definition of the amines also to be used as starting substances.

The starting substances of the formula (III) are known organic synthesis chemicals and/or can be prepared by processes which are known per se.

If appropriate, the process according to the invention is carried out in the presence of a suitable acid acceptor. Possible acid acceptors are all the customary inorganic or organic bases. These include, for example, alkaline earth metal or alkali metal hydrides, hydroxides, amides, alcoholates, acetates, carbonates or bicarbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium bicarbonate, sodium bi-carbonate or ammonium carbonate, and tertiary amines, such as trimethylamine, triethylamine, tributylamine, N,N-dimethylaniline, N,N-dimethyl-benzylamine, pyridine, N-methylpiperidine, N,N-dimethylaminopyridine, diazabicyclooctane (DABCO), diazabicyclononene (DBN) or diazabicycloundecene (DBU).

If appropriate, the process according to the invention is carried out in the presence of a suitable condensing agent. Possible condensing agents are all the condensing agents which can usually be used for such amidation reactions. Examples which may be mentioned are agents which form acid halide, such as phosgene, phosphorus tribromide, phosphorus trichloride, phosphorus pentachloride, phosphorus oxychloride or thionyl chloride; agents which form anhydrides, such as ethyl chloroformate, methyl chloroformate or methanesulphonyl chloride; carbodiimides, such as N,N'-dicyclohexylcarbodiimide (DCC), or other customary condensing agents, such as phosphorus pentoxide, polyphosphoric acid, N,N'-carbonyldiimidazole, 2-ethoxy-N-ethoxycarbonyl-1,2-dihydroquinoline (EEDQ) or triphenylphosphine/carbon tetrachloride.

If appropriate, the process according to the invention is carried out in the presence of a diluent. Possible diluents for carrying out the process according to the invention are water and organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric acid triamide; esters, such as methyl acetate or ethyl acetate, sulphoxides, such as dimethyl sulphoxide, alcohols, such as methanol, ethanol, n- or i-propanol, ethylene glycol, ethylene glycol monomethyl ether, ethylene glycol monoethyl ether, diethylene glycol monomethyl ether or diethylene glycol monoethyl ether, or mixtures thereof with water, or pure water.

The reaction temperatures can be varied within a substantial range in carrying out the process according to the invention. The process is in general carried out at temperatures between −20° C. and +200° C., preferably at temperatures between 0° C. and 150° C.

For carrying out the process according to the invention, in general 1 to 5 mol, preferably 1.0 to 2.5 mol, of amine are employed per mol of carboxylic acid derivative of the formula (II).

The reaction is carried out and the reaction products are worked up and isolated by known processes (cf. the preparation examples).

If appropriate, the process according to the invention is carried out in the presence of a catalyst. Examples which may be mentioned are 4-dimethylaminopyridine, 1-hydroxy-benzotriazole or dimethylformamide.

The reaction temperatures can be varied within a substantial range in carrying out the process according to the invention. The process is in general carried out at temperatures between −78° C. and +120° C., preferably at temperatures between −60° C. and +25° C.

For carrying out the process according to the invention for the preparation of the compounds of the formula (I), in general 0.5 to 5 mol, preferably equimolar amounts, of amine of the formula (III) are employed per mol of the alkoximinoacetic acid derivative of the formula (II).

The reaction is carried out and the reaction products are worked up and isolated by known processes (cf. the preparation examples).

The process according to the invention can also be carried out as a two-stage process. In this case, the carboxylic acid derivatives of the general formula (II) are first converted into an activated form and are reacted with the amines of the general formula (III) in a subsequent step to give the alkoximinoacetic acid derivatives of the general formula (I) according to the invention.

Possible activated forms of the carboxylic acid derivatives of the formula (II) are all the carboxyl-activated derivatives, such as, for example, acid halides, preferably acid chlorides, acid azides and furthermore symmetric and mixed anhydrides, such as, for example, mixed 0-alkylcarbonic acid anhydrides, and furthermore activated esters, such as, for example, p-nitrophenyl esters or N-hydroxy-succinimide esters, as well as adducts with condensing agents, such as, for example, dicyclohexylcarbodiimide, or activated forms of the carboxylic acids produced in situ.

The active compounds according to the invention have a potent microbicidal action and are employed in practice for combating undesirable microorganisms. The active compounds are particularly suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, Pythium ultimum;

Phytophthora species, such as, for example, Phytophthora infestans;

Pseudoperonospora species, such as, for example, Pseudoperonospora humuli or Pseudoperonospora cubensis;

Plasmopara species, such as, for example, Plasmopara viticola;

Peronospora species, such as, for example, Peronospora pisi or Peronospora brassicae;

Erysiphe species, such as, for example, Erysiphe graminis;

Sphaerotheca species, such as, for example, Sphaerotheca fuliginea;

Podosphaera species, such as, for example, Podosphaera leucotricha;

Venturia species, such as, for example, Venturia inaequalis;

Pyrenophora species, such as, for example, Pyrenophora teres or Pyrenophora graminea (conidia form: Drechslera, syn: Helminthosporium);

Cochliobolus species, such as, for example, Cochliobolus sativus (conidia form: Drechslera, syn: Helminthosporium);

Uromyces species, such as, for example, Uromyces appendiculatus;

Puccinia species, such as, for example, Puccinia recondita;

Tilletia species, such as, for example, Tilletia caries;

Ustilago species, such as, for example, Ustilago nuda or Ustilago avenae;

Pellicularia species, such as, for example, Pellicularia sasakii;

Pyricularia species, such as, for example, Pyricularia oryzae;

Fusarium species, such as, for example, Fusarium culmorum;

Botrytis species, such as, for example, Botrytis cinerea;

Septoria species, such as, for example, Septoria nodorum;

Leptosphaeria species, such as, for example, Leptosphaeria nodorum;

Cercospora species, such as, for example, Cercospora canescens;

Alternaria species, such as, for example, Alternaria brassicae and

Pseudocercosporella species, such as, for example, Pseudocercosporella herpotrichoides.

The good toleration by plants of the active compounds, at the concentrations required for combating plant diseases, permits treatment of above-ground parts of plants, of vegetative propagation stock and seeds, and of the soil.

The active compounds according to the invention are employed here with particularly good success for combating diseases in wine, fruit and vegetable growing, such as, for example, against Plasmopara and Phytophthora species.

Depending on their particular physical and/or chemical properties,

The active compounds can be converted into the customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospho-lipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds according to the invention are also used as such or in their formulations as a mixture with known fungicides, bactericides, acaricides, nematicides or insecticides, in order thus, for example, to increase the action spectrum or to prevent development of resistance.

In many cases, synergistic actions are observed here.

The following components are possible, for example, for the mixtures:

Fungicides 2-aminobutane; 2-anilino-4-methyl-6-cyclopropyl-pyrimidine; 2',6'-dibromo-2-methyl-4'-trifluoromethoxy-4'-trifluoro-methyl- 1,3 -thiazole-5-carboxanilide; 2,6-dichloro-N-(4-trifluoromethylbenzyl)benzamide; (E)-2-methoxyimino-N-methyl-2-(2-phenoxy- phenyl)acetamide; 8-hydroxyquinoline sulphate; methyl (E)-2-{2-[6-(2-cyano-phenoxy)pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, chinomethionate (quinomethionate), chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper formulations, such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur formulations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper formulations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chloretoxyfos chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamdon, phoxim, pirimicarb, pirimiphos M, pirimiphos A, profenofos, profenophos, promecarb, propaphos, propoxur, prothiofos, prothiophos, prothoate, pymetrozin, pyrachlophos, pyraclofos, pyraclophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

If appropriate, the active compounds according to the invention are also mixed with other known active compounds, such as herbicides, or else with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

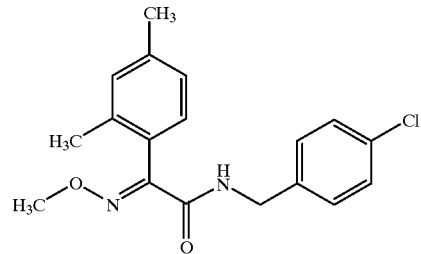

A mixture of 1.66 g (8 mmol) of methyl 2-methoximino-2-[2-(2,4-dimethyl)phenyl]acetate and 1.14 g (8 mmol) of 4-chlorobenzylamine is stirred at 120° C., in the melt for 12 hours. After cooling, it is taken up in methylene chloride and the mixture is washed with water, then with 1 N hydrochloric acid and then again with water, dried over sodium sulphate and filtered. The filtrate is concentrated in vacuo and the residue is chromatographed with petroleum ether/ethyl acetate (5:1) over silica gel.

1.24 g (47% of theory) of N-(4-chlorobenzyl)-2-methoximino-2-[2-(2,4-dimethyl)phenyl]-acetamide are obtained as an oil.

$^1$H—NMR (CDCl$_3$, TMS): δ=3.95 ppm (s,3 H)

Example 2

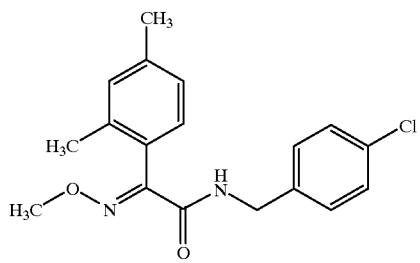

2.8 ml (20 mmol) of triethylamine and 2.8 g (20 mmol) of isobutyl chloroformate are added dropwise in succession to a solution of 4.14 g (20 mol) of 2-methoximino-2-[2-(2,4-dimethyl)phenyl]-acetic acid in 80 ml of methylene chloride at −10° C. and the mixture is stirred at −10° C. for 2 hours. A solution of 2.55 g (20 mmol) of 4-chloroaniline in 10 ml of methylene chloride is then added dropwise in the course of 30 minutes, and the mixture is stirred at −10° C. for 2 hours and at 20° C. for a further 18 hours. It is concentrated in vacuo, the residue is taken up in methylene chloride and the mixture is washed once with water, then with 1 N hydrochloric acid and then again with water, dried over sodium sulphate, filtered and concentrated again. The residue is stirred with diisopropyl ether and the crystals thus obtained are filtered off and dried.

3.8 g (60% of theory) of N-4-chlorophenyl-2-methoximino-2-[2-(2,4-dimethyl)phenyl]-acetamide of melting point 121° C. are obtained.

Example 3

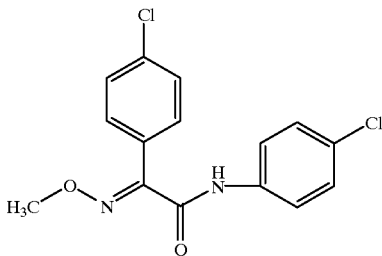

1.81 g (8 mmol) of 2-methoximino-2-(4-chlorophenyl)-acetyl chloride are added dropwise to a mixture of 1.02 g (8 mmol) of 4-chloroaniline and 1.12 ml (8 mmol) of triethylamine in 30 ml of methylene chloride at 20° C. in the course of 20 minutes and the mixture is stirred at 20° C. for 18 hours. It is poured onto water and washed first with sodium bicarbonate solution and then with water. The organic phase is dried over sodium sulphate, filtered and concentrated again. The residue is chromatographed with petroleum ether/ethyl acetate (5:1) on silica gel.

1.3 g (41% of theory) of N-(4-chlorophenyl)-2-methoximino-2-(4-chlorophenyl)-acetamide of melting point 105° C. are obtained.

Example 4

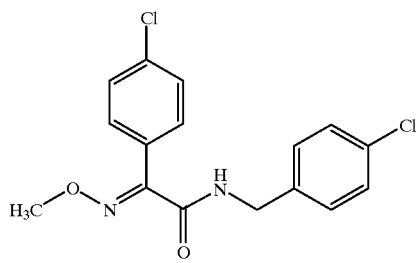

4.45 g (20 mmol) of methyl 2-methoximino-2-(4-chlorophenyl)-acetate in 50 ml of methanol are initially introduced into the reaction vessel and 2.83 g (20 mmol) of 4-chlorobenzylamine and 7.2 g (40 mmol) of 30% strength methanolic sodium methylate solution are added in succession at room temperature. The mixture is stirred at 65° C. for 20 hours, the solvent is then distilled off, the residue is taken up in methylene chloride and the mixture is washed successively with water, dilute hydrochloric acid and water and dried over sodium sulphate. After the solvent has been distilled off, the residue is chromatographed with petroleum ether/ethyl acetate (10:1) on silica gel.

3.4 g (51% of theory) of N-(4-chlorobenzyl)-2-methoximino-2-(4-chlorophenyl)-acetamide are obtained.

$^1$H—NMR (DCDl$_3$, TMS): δ=3.98 ppm (s,3 H)

The compounds listed in the following Table 7 can also be prepared, for example, analogously to Examples 1 to 4 and in accordance with the general description of the preparation process according to the invention:

TABLE 7

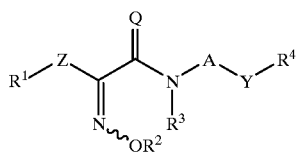

Ia

| Compound No. | $R^1$ | Z | E/Z-isomer | $R^2$ | Q | $R^3$ | A | Y | $R^4$ | physical constant |
|---|---|---|---|---|---|---|---|---|---|---|
| 5 | H | Ph | Z | CH$_3$ | O | H | CH(CH$_3$)(R+) | Ph | 4-Cl | log p: 3.69 |
| 6 | H | Ph | E | CH$_3$ | O | H | CH(CH$_3$)(R+) | Ph | 4-Cl | Mp. 59° C. |
| 7 | H | Ph | Z | CH$_3$ | O | H | CH$_2$ | Ph | 4-Cl | Mp. 102° C. |
| 8 | H | Ph | Z | CH$_3$ | O | H | — | Ph | 4-Cl | Mp. 93° C. |
| 9 | H | Ph | Z | CH$_3$ | O | H | CH(CH$_3$) | Ph | 4-CH$_3$ | Mp. 43° C. |

TABLE 7-continued

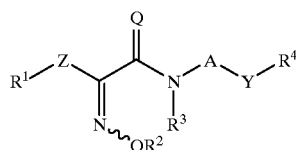

Ia

| Compound No. | R¹ | Z | E/Z-isomer | R² | Q | R³ | A | Y | R⁴ | physical constant |
|---|---|---|---|---|---|---|---|---|---|---|
| 10 | H | Ph | E | CH₃ | O | H | CH₂ | Ph | 4-Cl | Mp. 75° C. |
| 11 | H | Ph | E | CH₃ | O | H | CH(CH₃) | Ph | 4-CH₃ | Mp. 55° C. |
| 12 | H | Ph | E | CH₃ | O | H | — | Ph | 4-Cl | Mp. 194° C. |
| 13 | H | Ph | E/Z | CH₃ | O | H | — | Cyclohexyl | H | Mp. 116° C. |
| 14 | H | Ph | E/Z | CH₃ | O | H | — | 2-Pyridyl | H | Mp. 63° C. |
| 15 | H | Ph | E/Z | CH₃ | O | H | — | 2,6-Pyrimidinyl | H | log p: 1.65 |
| 16 | H | Ph | E | CH₃ | O | H | — | Cyclohexyl | H | Mp. 135° C. |
| 17 | H | Ph | E/Z | CH₃ | O | H | C(CH₃)(CN) | Ph | 4-Cl | Mp. 181° C. |
| 18 | H | Ph | Z | CH₃ | O | H | — | 2,6-Pyrimidinyl | 3,5-(CH₃)₂ | NMR: 3.93(s, 3H) |
| 19 | 4-Cl | Ph | Z | CH₃ | O | H | CH(CH₃) | Ph | 4-Cl | log p: 3.95 |
| 20 | 4-Cl | Ph | Z | CH₃ | O | H | — | Cyclohexyl | H | Mp. 62° C. |
| 21 | 4-Cl | Ph | E | CH₃ | O | H | CH(CH₃) | Ph | 4-Cl | log p: 3.68 |
| 22 | 4-Cl | Ph | E | CH₃ | O | H | — | Cyclohexyl | H | Mp. 166° C. |
| 23 | 2,4-(CH₃)₂ | Ph | E/Z | CH₃ | O | H | CH(CH₃)(R+) | Ph | 4-Cl | log p: 3.95 |
| 24 | 4-Cl | Ph | E | CH₃ | O | H | CH₂—CH₂ | Ph | 3,4-(OCH₃)₂ | log p: 2.99 |
| 25 | H | Ph | E/Z | CH₃ | O | H | CH₂—CH₂ | Ph | 3,4-(OCH₃)₂ | log p: 2.27/2.50 |
| 26 | H | Ph | E | CH₃ | O | H | — | 2,6-Pyrimidinyl | 3,5-(CH₃)₂ | NMR: 4.07(s, 3H) |
| 27 | 2,4-Cl₂ | Ph | E/Z | CH₃ | O | H | — | 2,6-Pyrimidinyl | 3,5-(CH₃)₂ | log p: 2.46/2.86 |
| 28 | 2,4-Cl₂ | Ph | E/Z | CH₃ | O | H | CH₂—CH₂ | Ph | 3,4-(OCH₃)₂ | log p: 3.19/3.31 |
| 29 | 4-Cl | Ph | Z | CH₃ | O | H | — | Ph | 4-Cl | Mp. 112° C. |
| 30 | 2,4-Cl₂ | Ph | E/Z | CH₃ | O | H | — | Ph | 4-Cl | Mp. 141° C. |
| 31 | 2,4-Cl₂ | Ph | E/Z | CH₃ | O | H | CH₂ | Ph | 4-Cl | Mp. 109° C. |
| 32 | 2,4-Cl₂ | Ph | E/Z | CH₃ | O | H | CH(CH₃)(R+) | Ph | 4-Cl | log p: 4.02/4.15 |
| 33 | 2,4-(CH₃)₂ | Ph | E/Z | CH₃ | O | H | — | Cyclohexyl | H | Mp. 72° C. |
| 34 | 2,4-Cl₂ | Ph | E/Z | CH₃ | O | H | — | Cyclohexyl | H | Mp. 90° C. |
| 35 | 2,4-Cl₂ | Ph | E/Z | CH₃ | O | H | — | Ph | 2-i-Propyl | log p: 4.32/4.47 |
| 36 | 2,4-Cl₂ | Ph | E/Z | CH₃ | O | H | — | Ph | 2-Cyclohexyl | Mp. 79° C. |
| 37 | 2,4-(CH₃)₂ | Ph | E | CH₃ | O | H | — | Ph | 2-s-Butyl | log p: 4.65 |
| 38 | 2,4-(CH₃)₂ | Ph | Z | CH₃ | O | H | — | Ph | 2-s-Butyl | NMR: 4.13(s, 3H) |
| 39 | H | Ph | Z | CH₃ | O | H | CH₂—CH₂ | Ph | 3,4-(OCH₃)₂ | log P: 2.50 |
| 40 | H | Ph | E | CH₃ | O | H | CH₂—CH₂ | Ph | 3,4-(OCH₃)₂ | log p: 2.26 |
| 41 | 4-CH₃ | Ph | E/Z | CH₃ | O | H | CH₂—CH₂ | Ph | 3,4-(OCH₃)₂ | log p: 2.53/2.77 |
| 42 | 4-CH₃ | Ph | E | CH₃ | O | H | CH₂—CH₂ | Ph | 3,4-(OCH₃)₂ | Mp. 72° C. |
| 43 | 4-CH₃ | Ph | Z | CH₃ | O | H | CH₂—CH₂ | Ph | 4-F | Mp. 44° C. |
| 44 | 4-CH₃ | Ph | Z | CH₃ | O | H | CH₂—CH₂ | Ph | 3-Cl | log p: 3.63 |
| 45 | 4-CH₃ | Ph | Z | CH₃ | O | H | CH₂—CH₂ | Ph | 3-OCH₃ | log p: 3.20 |
| 46 | 4-CH₃ | Ph | Z | CH₃ | O | H | CH₂—CH₂ | Ph | 2,4-Cl₂ | log p: 4.15 |
| 47 | 4-CH₃ | Ph | Z | CH₃ | O | H | CH₂—CH₂ | Ph | 4-OCH₃ | log p: 3.16 |
| 48 | 4-CH₃ | Ph | E/Z | CH₃ | O | H | — | Ph | 3,4-(OCH₃)₂ | log p: 2.59/2.91 |
| 49 | 4-CH₃ | Ph | E | CH₃ | O | H | CH₂—CH₂ | Ph | 4-F | Mp. 71° C. |
| 50 | 4-CH₃ | Ph | E | CH₃ | O | H | CH₂—CH₂ | Ph | 3-OCH₃ | Mp. 94° C. |
| 51 | 4-CH₃ | Ph | E | CH₃ | O | H | CH₂—CH₂ | Ph | 4-OCH₃ | Mp. 85° C. |
| 52 | 4-CH₃ | Ph | Z | CH₃ | O | H | CH₂—CH₂ | Ph | 2-OCH₃ | log p: 3.40 |
| 53 | 4-CH₃ | Ph | Z | CH₃ | O | H | CH₂—CH₂ | Ph | 3-F | log p: 3.20 |
| 54 | 4-OCH₃ | Ph | E | CH₃ | O | H | CH₂—CH₂ | Ph | 3,4-(OCH₃)₂ | log p: 2.25 |
| 55 | 4-CH₃ | Ph | Z | CH₃ | O | H | CH₂—CH₂ | Ph | 3,4-(OCH₃)₂ | log p: 2.50 |
| 56 | 4-CH₃ | Ph | Z | CH₃ | O | H | CH₂—CH₂ | Ph | 2-Cl | log p: 3.64 |
| 57 | 4-CH₃ | Ph | E | CH₃ | O | H | CH₂—CH₂ | Ph | 2,4-Cl₂ | Mp. 101° C. |
| 58 | 4-CH₃ | Ph | E | CH₃ | O | H | CH₂—CH₂ | Ph | 3-Cl | Mp. 103° C. |
| 59 | 4-CH₃ | Ph | Z | CH₃ | O | H | CH₂—CH₂ | Ph | 4-Cl | Mp. 75° C. |
| 60 | 4-CH₃ | Ph | Z | CH₃ | O | H | CH₂—CH₂ | Ph | H | log p: 3.26 |
| 61 | 4-CH₃ | Ph | Z | CH₃ | O | CH₃ | CH₂—CH₂ | Ph | H | log p: 3.57 |
| 62 | 4-CH₃ | Ph | E | CH₃ | O | H | CH₂—CH₂ | Ph | 2-OCH₃ | Mp. 94° C. |
| 63 | 4-CH₃ | Ph | E | CH₃ | O | H | CH₂—CH₂ | Ph | 3-F | Mp. 92° C. |
| 64 | 4-CH₃ | Ph | Z | CH₃ | O | H | CH₂—CH₂ | Ph | 2,5-(OCH₃)₂ | log p: 3.75 |
| 65 | 4-CH₃ | Ph | Z | CH₃ | O | H | CH₂—CH₂ | Ph | 4-Br | Mp. 44° C. |
| 66 | 4-CH₃ | Ph | E/Z | CH₃ | O | H | CH₂ | Ph | 3,4-(OCH₃)₂ | NMR: 2.35(s, 3H) |
| 67 | 4-CH₃ | Ph | Z | CH₃ | O | CH₃ | CH₂—CH₂ | Ph | 3,4-(OCH₃)₂ | log p: 3.03 |
| 68 | 4-CH₃ | Ph | E | CH₃ | O | H | CH₂—CH₂ | Ph | H | Mp. 85° C. |
| 69 | 4-CH₃ | Ph | E | CH₃ | O | H | CH₂—CH₂ | Ph | 2-Cl | Mp. 93° C. |
| 70 | 4-CH₃ | Ph | E | CH₃ | O | H | CH₂—CH₂ | Ph | 4-Cl | Mp. 104° C. |
| 71 | 4-CH₃ | Ph | E | CH₃ | O | H | CH₂—CH₂ | Ph | 4-Br | Mp. 122° C. |
| 72 | 5-CH₃ | 2-Thienyl | Z | CH₃ | O | H | CH₂—CH₂ | Ph | 3,4-(OCH₃)₂ | Mp. 79° C. |
| 73 | 5-CH₃ | 2-Thienyl | E | CH₃ | O | H | CH₂—CH₂ | Ph | 3,4-(OCH₃)₂ | log p: 2.46 |
| 74 | 4-CH₃ | Ph | E | CH₃ | O | CH₃ | CH₂—CH₂ | Ph | 3,4-(OCH₃)₂ | log P: 2.86 |

TABLE 7-continued

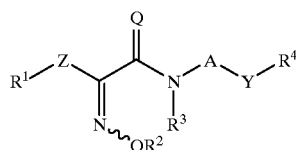

| Compound No. | $R^1$ | Z | E/Z-isomer | $R^2$ | Q | $R^3$ | A | Y | $R^4$ | physical constant |
|---|---|---|---|---|---|---|---|---|---|---|
| 75 | 4-$CH_3$ | Ph | E | $CH_3$ | O | $CH_3$ | $CH_2$—$CH_2$ | Ph | H | log p: 3.45 |
| 76 | 4-$CH_3$ | Ph | E | $CH_3$ | O | H | $CH_2$—$CH_2$ | Ph | 2,5-$(OCH_3)_2$ | log p: 3.04 |
| 77 | 4-Cl | Ph | E/Z | $C_2H_5$ | O | H | $CH_2$—$CH_2$ | Ph | 3,4-$(OCH_3)_2$ | log p: 3.07/3.34 |
| 78 | 4-$OC_2H_5$ | Ph | Z | $CH_3$ | O | H | $CH_2$—$CH_2$ | Ph | 3,4-$(OCH_3)_2$ | log p: 2.83 |
| 79 | 4-Cl | Ph | E/Z | H | O | H | $CH_2$—$CH_2$ | Ph | 3,4-$(OCH_3)_2$ | NMR: 3.87(s, 3H) |
| 80 | 4-$C_2H_5$ | Ph | Z | $CH_3$ | O | H | $CH_2$—$CH_2$ | Ph | 3,4-$(OCH_3)_2$ | NMR: 3.95(s, 3H) |
| 81 | 4-$C_2H_5$ | Ph | E | $CH_3$ | O | H | $CH_2$—$CH_2$ | Ph | 3,4-$(OCH_3)_2$ | log p: 2.86 |
| 82 | 4-$OC_2H_5$ | Ph | E | $CH_3$ | O | H | $CH_2$—$CH_2$ | Ph | 3,4-$(OCH_3)_2$ | log p: 2.59 |
| 83 | 4-$CH(CH_3)_2$ | Ph | Z | $CH_3$ | O | H | $CH_2$—$CH_2$ | Ph | 3,4-$(OCH_3)_2$ | NMR: 3.88(s, 3H) |
| 84 | 4-$CH(CH_3)_2$ | Ph | E | $CH_3$ | O | H | $CH_2$—$CH_2$ | Ph | 3,4-$(OCH_3)_2$ | NMR: 3.81(s, 3H) |
| 85 | 5-$CH_3$ | 2-Furanyl | E/Z | $CH_3$ | O | H | $CH_2$—$CH_2$ | Ph | 3,4-$(OCH_3)_2$ | log p: 2.04/2.26 |
| 86 | 4-$CH_3$ | 2-Thienyl | Z | $CH_3$ | O | H | $CH_2$—$CH_2$ | Ph | 3,4-$(OCH_3)_2$ | log p: 2.85 |
| 87 | 4-$CH_3$ | 2-Thienyl | E | $CH_3$ | O | H | $CH_2$—$CH_2$ | Ph | 3,4-$(OCH_3)_2$ | log p: 2,54 |
| 88 | 5-$CH_3$ | 2-Furanyl | E | $CH_3$ | O | H | $CH_2$—$CH_2$ | Ph | 3,4-$(OCH_3)_2$ | log p: 2.04 |
| 89 | 5-$CH_3$ | 2-Furanyl | Z | $CH_3$ | O | H | $CH_2$—$CH_2$ | Ph | 3,4-$(OCH_3)_2$ | log p: 2.26 |
| 90 | 5-$OCH_3$ | 2-Thienyl | E/Z | $CH_3$ | O | H | $CH_2$—$CH_2$ | Ph | 3,4-$(OCH_3)_2$ | log p: 2.04/2.14 |
| 91 | 3,4-$(CH_3)_2$ | Ph | Z | $CH_3$ | O | H | $CH_2$—$CH_2$ | Ph | 3,4-$(OCH_3)_2$ | log p: 3.00 |
| 92 | 4-$C(CH_3)_3$ | Ph | Z | $CH_3$ | O | H | $CH_2$—$CH_2$ | Ph | 3,4-$(OCH_3)_2$ | log p: 3.72 |
| 93 | 4-F | Ph | Z | $CH_3$ | O | H | $CH_2$—$CH_2$ | Ph | 3,4-$(OCH_3)_2$ | log p: 2.61 |
| 94 | 4-Br | Ph | Z | $CH_3$ | O | H | $CH_2$—$CH_2$ | Ph | 3,4-$(OCH_3)_2$ | log p: 3.08 |
| 95 | 4-Cl | 2-Thienyl | Z | $CH_3$ | O | H | $CH_2$—$CH_2$ | Ph | 3,4-$(OCH_3)_2$ | log p: 2.56 |
| 96 | 4-Br | Ph | E | $CH_3$ | O | H | $CH_2$—$CH_2$ | Ph | 3,4-$(OCH_3)_2$ | log p: 2.82 |
| 97 | 5-Cl | 2-Thienyl | Z | $CH_3$ | O | H | $CH_2$—$CH_2$ | Ph | 3,4-$(OCH_3)_2$ | Mp.: 91° C. |
| 98 | 4-F | Ph | E | $CH_3$ | O | H | $CH_2$—$CH_2$ | Ph | 3,4-$(OCH_3)_2$ | log p: 2.39 |
| 99 | 3,4-$(CH_3)_2$ | Ph | E | $CH_3$ | O | H | $CH_2$—$CH_2$ | Ph | 3,4-$(OCH_3)_2$ | log p: 2.75 |
| 100 | H | 3-Indolyl | E/Z | $CH_3$ | O | H | $CH_2$—$CH_2$ | Ph | 3,4-$(OCH_3)_2$ | log p: 2.21/2.28 |
| 101 | 3,4-$Cl_2$ | Ph | Z | $CH_3$ | O | H | $CH_2$—$CH_2$ | Ph | 3,4-$(OCH_3)_2$ | log p: 3.43 |
| 102 | 4-$C(CH_3)_3$ | Ph | E | $CH_3$ | O | H | $CH_2$—$CH_2$ | Ph | 3,4-$(OCH_3)_2$ | log p: 3.39 |
| 103 | 5-Cl | 2-Thienyl | E | $CH_3$ | O | H | $CH_2$—$CH_2$ | Ph | 3,4-$(OCH_3)_2$ | Fp: 98° C. |
| 104 | 4-$CH_3$ | Ph | Z | $C_2H_5$ | O | H | $CH_2$—$CH_2$ | Ph | 3,4-$(OCH_3)_2$ | log p: 3.13 |
| 105 | 4-$NO_2$ | Ph | E/Z | $CH_3$ | O | H | $CH_2$—$CH_2$ | Ph | 3,4-$(OCH_3)_2$ | log p: 2.45/2.66 |
| 106 | 3,4-$(OCH_3)_2$ | Ph | Z | $CH_3$ | O | H | $CH_2$—$CH_2$ | Ph | 3,4-$(OCH_3)_2$ | log p: 2.21 |
| 107 | 4-Cl | 2-Thienyl | E | $CH_3$ | O | H | $CH_2$—$CH_2$ | Ph | 3,4-$(OCH_3)_2$ | Mp. 88° C. |
| 108 | 3,4-$Cl_2$ | Ph | E | $CH_3$ | O | H | $CH_2$—$CH_2$ | Ph | 3,4-$(OCH_3)_2$ | Mp. 122° C. |
| 109 | 4-$SO_2CH_3$ | Ph | E/Z | $CH_3$ | O | H | $CH_2$—$CH_2$ | Ph | 3,4-$(OCH_3)_2$ | Mp. 94° C. |
| 110 | 4-$CH_3$ | Ph | E | $C_2H_5$ | O | H | $CH_2$—$CH_2$ | Ph | 3,4-$(OCH_3)_2$ | log p: 2.85 |
| 111 | H | 2-Benzo-thienyl | E/Z | $CH_3$ | O | H | $CH_2$—$CH_2$ | Ph | 3,4-$(OCH_3)_2$ | log p: 2.84/2.91 |
| 112 | H | 2-Napthyl | E/Z | $CH_3$ | O | H | $CH_2$—$CH_2$ | Ph | 3,4-$(OCH_3)_2$ | Fp: 64° C. |
| 113 | 3,4-$(OCH_3)_2$ | Ph | E | $CH_3$ | O | H | $CH_2$—$CH_2$ | Ph | 3,4-$(OCH_3)_2$ | Mp. 122° C. |
| 114 | 3,4-$(CH_2)_3$— | Ph | Z | $CH_3$ | O | H | $CH_2$—$CH_2$ | Ph | 3,4-$(OCH_3)_2$ | log p: 3.01 |
| 115 | 4-$(CH_2)_2CH_3$ | Ph | Z | $CH_3$ | O | H | $CH_2$—$CH_2$ | Ph | 3,4-$(OCH_3)_2$ | log p: 3.53 |
| 116 | 4-$C_2H_5$ | Ph | Z | $C_2H_5$ | O | H | $CH_2$—$CH_2$ | Ph | 3,4-$(OCH_3)_2$ | Mp. 66° C. |
| 117 | 3,4-$(CH_2)_4$— | Ph | Z | $CH_3$ | O | H | $CH_2$—$CH_2$ | Ph | 3,4-$(OCH_3)_2$ | log p: 3.44 |
| 118 | 4-$CH_2CH(CH_3)_2$ | Ph | Z | $CH_3$ | O | H | $CH_2$—$CH_2$ | Ph | 3,4-$(OCH_3)_2$ | log p: 3.87 |
| 119 | 5-Br | 2-Thienyl | Z | $CH_3$ | O | H | $CH_2$—$CH_2$ | Ph | 3,4-$(OCH_3)_2$ | Mp. 80° C. |
| 120 | 4-OPh | Ph | Z | $CH_3$ | O | H | $CH_2$—$CH_2$ | Ph | 3,4-$(OCH_3)_2$ | Mp. 42° C. |
| 121 | 4-$(CH_2)_2CH_3$ | Ph | Z | $CH_3$ | O | H | $CH_2$—$CH_2$ | Ph | 3,4-$(OCH_3)_2$ | log p. 3.91 |
| 122 | 4-$C_2H_5$ | Ph | E | $C_2H_5$ | O | H | $CH_2$—$CH_2$ | Ph | 3,4-$(OCH_3)_2$ | Mp. 82° C. |
| 123 | 3,4-$(CH_2)_3$— | Ph | E | $CH_3$ | O | H | $CH_2$—$CH_2$ | Ph | 3,4-$(OCH_3)_2$ | Mp. 98° C. |
| 124 | 4-$(CH_2)_2CH_3$ | Ph | E | $CH_3$ | O | H | $CH_2$—$CH_2$ | Ph | 3,4-$(OCH_3)_2$ | log p: 3.25 |
| 125 | 4-$CH_2CH(CH_3)_2$ | Ph | E | $CH_3$ | O | H | $CH_2$—$CH_2$ | Ph | 3,4-$(OCH_3)_2$ | log p: 3.58 |
| 126 | 4-$OCH_2Ph$ | Ph | Z | $CH_3$ | O | H | $CH_2$—$CH_2$ | Ph | 3,4-$(OCH_3)_2$ | log p: 3.49 |
| 127 | 5-$C_2H_5$ | 2-Thienyl | Z | $CH_3$ | O | H | $CH_2$—$CH_2$ | Ph | 3,4-$(OCH_3)_2$ | log p: 3.22 |
| 128 | 4-Ph | Ph | Z | $CH_3$ | O | H | $CH_2$—$CH_2$ | Ph | 3,4-$(OCH_3)_2$ | log p: 3.50 |
| 129 | 4-OPh | Ph | E | $CH_3$ | O | H | $CH_2$—$CH_2$ | Ph | 3,4-$(OCH_3)_2$ | log p: 3.24 |
| 130 | 5-Br | 2-Thienyl | E | $CH_3$ | O | H | $CH_2$—$CH_2$ | Ph | 3,4-$(OCH_3)_2$ | log p: 2.87 |
| 131 | 3,4-$(CH_2)_4$— | Ph | E | $CH_3$ | O | H | $CH_2$—$CH_2$ | Ph | 3,4-$(OCH_3)_2$ | Mp. 100° C. |
| 132 | 4-$(CH_2)_3CH_3$ | Ph | E | $CH_3$ | O | H | $CH_2$—$CH_2$ | Ph | 3,4-$(OCH_3)_2$ | log p: 3.62 |
| 133 | 4-$OCH_2Ph$ | Ph | E | $CH_3$ | O | H | $CH_2$—$CH_2$ | Ph | 3,4-$(OCH_3)_2$ | Mp. 123° C. |
| 134 | H | 2-Thienyl | Z | $CH_3$ | O | H | $CH_2$—$CH_2$ | Ph | 3,4-$(OCH_3)_2$ | Mp. 81° C. |
| 135 | 3,4-$(C_2H_5)_2$ | Ph | Z | $CH_3$ | O | H | $CH_2$—$CH_2$ | Ph | 3,4-$(OCH_3)_2$ | log p: 3.67 |
| 136 | 4-Ph | Ph | E | $CH_3$ | O | H | $CH_2$—$CH_2$ | Ph | 3,4-$(OCH_3)_2$ | Mp. 110° C. |

TABLE 7-continued

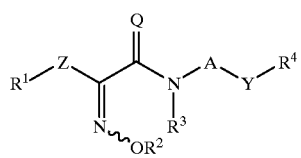

Ia

| Compound No. | R¹ | Z | E/Z-isomer | R² | Q | R³ | A | Y | R⁴ | physical constant |
|---|---|---|---|---|---|---|---|---|---|---|
| 137 | 4-SCH₃ | Ph | Z | CH₃ | O | H | CH₂—CH₂ | Ph | 3,4-(OCH₃)₂ | log p: 2.86 |
| 138 | 4-CH(CH₃)C₂H₅ | Ph | Z | CH₃ | O | H | CH₂—CH₂ | Ph | 3,4-(OCH₃)₂ | log p: 3.82 |
| 139 | 4-Br | Ph | E/Z | C₂H₅ | O | H | CH₂—CH₂ | Ph | 3,4-(OCH₃)₂ | log p: 3.15/3.43 |
| 140 | 3,4-OCH₂O— | Ph | Z | CH₃ | O | H | CH₂—CH₂ | Ph | 3,4-(OCH₃)₂ | log p: 2.40 |
| 141 | 3,4-O(CH₂)₂O— | Ph | Z | CH₃ | O | H | CH₂—CH₂ | Ph | 3,4-(OCH₃)₂ | log p: 2.41 |
| 142 | 4-SCH₃ | Ph | E | CH₃ | O | H | CH₂—CH₂ | Ph | 3,4-(OCH₃)₂ | Mp. 98° C. |
| 143 | 5-C₂H₅ | 2-Thienyl | E | CH₃ | O | H | CH₂—CH₂ | Ph | 3,4-(OCH₃)₂ | log p: 2.77 |
| 144 | 3,4-(C₂H₅)₂ | Ph | E | CH₃ | O | H | CH₂—CH₂ | Ph | 3,4-(OCH₃)₂ | Mp. 78° C. |
| 145 | 4-CH(CH₃)C₂H₅ | Ph | E | CH₃ | O | H | CH₂—CH₂ | Ph | 3,4-(OCH₃)₂ | log p: 3.52 |
| 146 | 4-Br | Ph | E | C₂H₅ | O | H | CH₂—CH₂ | Ph | 3,4-(OCH₃)₂ | log p: 3.15 |
| 147 | 3,4-O(CH₂)O— | Ph | E | CH₃ | O | H | CH₂—CH₂ | Ph | 3,4-(OCH₃)₂ | Mp. 134° C. |
| 148 | 3,4-F₂ | Ph | Z | CH₃ | O | H | CH₂—CH₂ | Ph | 3,4-(OCH₃)₂ | log p: 2.59 |
| 149 | 3,4-O(CH₂)₂O— | Ph | E | CH₃ | O | H | CH₂—CH₂ | Ph | 3,4-(OCH₃)₂ | log p: 2.19 |
| 150 | 4,5-Br₂ | 2-Thienyl | Z | CH₃ | O | H | CH₂—CH₂ | Ph | 3,4-(OCH₃)₂ | Mp. 104° C. |
| 151 | 4-(CH₂)₄CH₃ | Ph | Z | CH₃ | O | H | CH₂—CH₂ | Ph | 3,4-(OCH₃)₂ | log p: 4.34 |
| 152 | H | 2-Thienyl | E | CH₃ | O | H | CH₂—CH₂ | Ph | 3,4-(OCH₃)₂ | Mp. 92° C. |
| 153 | 4-Cyclopropyl | Ph | E/Z | CH₃ | O | H | CH₂—CH₂ | Ph | 3,4-(OCH₃)₂ | NMR: 3.88 (s, 3H) |
| 154 | 45-Br₂ | 2-Thienyl | E/Z | CH₃ | O | H | CH₂—CH₂ | Ph | 3,4-(OCH₃)₂ | NMR: 4.07 (s, 3H) |
| 155 | 4-(CH₂)₄CH₃ | Ph | E | CH₃ | O | H | CH₂—CH₂ | Ph | 3,4-(OCH₃)₂ | log p: 4.04 |
| 156 | 3,4-F₂ | Ph | E | CH₃ | O | H | CH₂—CH₂ | Ph | 3,4-(OCH₃)₂ | Mp. 104° C. |
| 157 | 41 Cyclopropyl | Ph | E | CH₃ | O | H | CH₂—CH₂ | Ph | 3,4-(OCH₃)₂ | NMR: 3.82(s, 3H) |
| 158 | 4-F,3-OCH₃ | Ph | Z | CH₃ | O | H | CH₂—CH₂ | Ph | 3,4-(OCH₃)₂ | log p: 2.50 |
| 159 | H | 1-Napthyl | E/Z | CH₃ | O | H | CH₂—CH₂ | Ph | 3,4-(OCH₃)₂ | Mp. 63° C. |
| 160 | 4-F,3-OCH₃ | Ph | E | CH₃ | O | H | CH₂—CH₂ | Ph | 3,4-(OCH₃)₂ | Mp. 102° C. |
| 161 | 4-OCH₃ | Ph | Z | C₂H₅ | O | H | CH₂—CH₂ | Ph | 3,4-(OCH₃)₂ | Mp. 43° C. |
| 162 | 4-Cyclohexyl | Ph | E/Z | CH₃ | O | H | CH₂—CH₂ | Ph | 3,4-(OCH₃)₂ | log p: 4.03/4.35 |
| 163 | 4-(CH₂)₅CH₃ | Ph | Z | CH₃ | O | H | CH₂—CH₂ | Ph | 3,4-(OCH₃)₂ | log p: 4.78 |
| 164 | 4-(CH₂)₆CH₃ | Ph | Z | CH₃ | O | H | CH₂—CH₂ | Ph | 3,4-(OCH₃)₂ | log p: 5.23 |
| 165 | 3,4-(CH₂)₃— | Ph | Z | C₂H₅ | O | H | CH₂—CH₂ | Ph | 3,4-(OCH₃)₂ | log p: 3.56 |
| 166 | 3,4-(CH₂)₄— | Ph | Z | C₂H₅ | O | H | CH₂—CH₂ | Ph | 3,4-(OCH₃)₂ | log p: 3.84 |
| 167 | 4-CH₃ | Ph | Z | CH₃ | O | H | CH₂—CH₂ | Ph | 3,4-(OCH₃)₂ | log p: 2.79 |
| 168 | 4-OCH₃ | Ph | E | C₂H₅ | O | H | CH₂—CH₂ | Ph | 3,4-(OCH₃)₂ | Mp. 86° C. |
| 169 | 4-(CH₂)₅CH₃ | Ph | E | CH₃ | O | H | CH₂—CH₂ | Ph | 3,4-(OCH₃)₂ | log p: 4.47 |
| 170 | 3,4-(CH₂)₃— | Ph | E | CH₃ | O | H | CH₂—CH₂ | Ph | 3,4-(OCH₃)₂ | log p: 3.25 |
| 171 | 4-Cyclohexyl | Ph | E | CH₃ | O | H | CH₂—CH₂ | Ph | 3,4-(OCH₃)₂ | log p: 4.03 |
| 172 | 4-(CH₂)₆CH₃ | Ph | E | CH₃ | O | H | CH₂—CH₂ | Ph | 3,4-(OCH₃)₂ | log p: 4.92 |
| 173 | 3,4-(CH₂)₄— | Ph | E | C₂H₅ | O | H | CH₂—CH₂ | Ph | 3,4-(OCH₃)₂ | log p: 3.53 |
| 174 | 3-Cl | Ph | E/Z | C₂H₅ | O | H | CH₂—CH₂ | Ph | 3,4-(OCH₃)₂ | log p: 3.08/3.30 |
| 175 | 4-OCF₃ | Ph | E/Z | CH₃ | O | H | CH₂—CH₂ | Ph | 3,4-(OCH₃)₂ | log p: 2.75/3.11 |
| 176 | 3-OCH₃ | Ph | Z | CH₃ | O | H | CH₂—CH₂ | Ph | 3,4-(OCH₃)₂ | log p: 2.03 |
| 177 | 4-CH₃ | Ph | E/Z | CH₂Ph | O | H | CH₂—CH₂ | Ph | 3,4-(OCH₃)₂ | log p: 3.47/3.69 |
| 178 | 4-Br | Ph | E/Z | CH₂Ph | O | H | CH₂—CH₂ | Ph | 3,4-(OCH₃)₂ | log p: 3.76/3.99 |
| 179 | 4-Cl | Ph | E/Z | CH₂Ph | O | H | CH₂—CH₂ | Ph | 3,4-(OCH₃)₂ | log p: 3.67/3.89 |
| 180 | 3,4-(CH₂)₄— | Ph | E/Z | CH₂Ph | O | H | CH₂—CH₂ | Ph | 3,4-(OCH₃)₂ | log p: 4.12/4.36 |
| 181 | 4-CH₃ | Ph | E/Z | C(CH₃)₃ | O | H | CH₂—CH₂ | Ph | 3,4-(OCH₃)₂ | log p: 3.58/3.79 |
| 182 | 4-CH₃ | Ph | E/Z | (CH₂)₂CH₃ | O | H | CH₂—CH₂ | Ph | 3,4-(OCH₃)₂ | log p: 3.20/3.50 |
| 183 | 4-CH₃ | Ph | E/Z | Allyl | O | H | CH₂—CH₂ | Ph | 3,4-(OCH₃)₂ | log p: 2.81/3.01 |
| 184 | 4-Cl | Ph | Z | (CH₂)₂CH₃ | O | H | CH₂—CH₂ | Ph | 3,4-(OCH₃)₂ | log p: 3.75 |
| 185 | 3,4-(CH₂)₃— | Ph | E/Z | C(CH₃)₃ | O | H | CH₂—CH₂ | Ph | 3,4-(OCH₃)₂ | log p: 3.98/4.19 |
| 186 | 3,4-(CH₂)₃— | Ph | E/Z | CH₂Ph | O | H | CH₂—CH₂ | Ph | 3,4-(OCH₃)₂ | log p: 3.85/4.06 |
| 187 | 3-OCH₃ | Ph | E | CH₃ | O | H | CH₂—CH₂ | Ph | 3,4-(OCH₃)₂ | log p: 2.01 |
| 188 | 3,4-(CH₂)₃— | Ph | E/Z | Allyl | O | H | CH₂—CH₂ | Ph | 3,4-(OCH₃)₂ | log p: 3.39/3.64 |
| 189 | 4-CH₃ | Ph | E/Z | CH(CH₃)₂ | O | H | CH₂—CH₂ | Ph | 3,4-(OCH₃)₂ | log p: 3.21/3.47 |
| 190 | 4-Cl | Ph | E/Z | (CH₂)₃CH₃ | O | H | CH₂—CH₂ | Ph | 3,4-(OCH₃)₂ | log p: 3.81/4.14 |
| 191 | 3,4-(CH₂)₃— | Ph | E/Z | (CH₂)₃CH₃ | O | H | CH₂—CH₂ | Ph | 3,4-(OCH₃)₂ | log p: 4.00/4.33 |
| 192 | 4-Cl | Ph | E/Z | Allyl | O | H | CH₂—CH₂ | Ph | 3,4-(OCH₃)₂ | log p: 3.22/3.47 |
| 193 | 3,4-(CH₂)₃— | Ph | E/Z | (CH₂)₂CH₃ | O | H | CH₂—CH₂ | Ph | 3,4-(OCH₃)₂ | log p: 3.62/3.92 |
| 194 | 3,4-(CH₂)₃— | Ph | E/Z | CH(CH₃)₂ | O | H | CH₂—CH₂ | Ph | 3,4-(OCH₃)₂ | log p: 3.64/3.89 |
| 195 | 4-C₂H₅ | Ph | E/Z | CH₂PH | O | H | CH₂—CH₂ | Ph | 3,4-(OCH₃)₂ | log p: 3.83/4.05 |
| 196 | 3,4-(CH₂)₄— | Ph | E/Z | H | O | H | CH₂—CH₂ | Ph | 3,4-(OCH₃)₂ | log p: 2.53/2.68 |
| 197 | 4-Br | Ph | E/Z | H | O | H | CH₂—CH₂ | Ph | 3,4-(OCH₃)₂ | log p: 2.32/2.38 |
| 198 | 3,4-(CH₂)₃ | Ph | E/Z | Propargyl | O | H | CH₂—CH₂ | Ph | 3,4-(OCH₃)₂ | NMR: 3.86(s, 3H) |
| 199 | 4-C₂H₅ | Ph | E/Z | H | O | H | CH₂—CH₂ | Ph | 3,4-(OCH₃)₂ | Mp.: 122° C. |

TABLE 7-continued

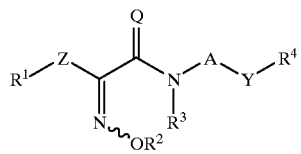

Ia

| Compound No. | R¹ | Z | E/Z-isomer | R² | Q | R³ | A | Y | R⁴ | physical constant |
|---|---|---|---|---|---|---|---|---|---|---|
| 200 | 3,4-(CH$_2$)$_3$ | Ph | E/Z | H | O | H | CH$_2$—CH$_2$ | Ph | 3,4-(OCH$_3$)$_2$ | Mp.: 115° C. |
| 201 | 4-CH$_3$ | Ph | E/Z | H | O | H | CH$_2$—CH$_2$ | Ph | 3,4-(OCH$_3$)$_2$ | Mp.: 143° C. |
| 202 | 3-CF$_3$ | Ph | E/Z | CH$_3$ | O | H | CH$_2$—CH$_2$ | Ph | 3,4-(OCH$_3$)$_2$ | log p: 2.99/3.21 |
| 203 | 3,4-(CH$_2$)$_3$ | Ph | E/Z | CH$_2$CN | O | H | CH$_2$—CH$_2$ | Ph | 3,4-(OCH$_3$)$_2$ | NMR: 3.87(s, 3H) |
| 204 | 4-CF$_3$ | Ph | E/Z | C$_2$H$_5$ | O | H | CH$_2$—CH$_2$ | Ph | 3,4-(OCH$_3$)$_2$ | log p: 3.32/3.58 |
| 205 | 4-CF$_3$ | Ph | E/Z | CH$_3$ | O | H | CH$_2$—CH$_2$ | Ph | 3,4-(OCH$_3$)$_2$ | log p: 3.01/3.25 |
| 206 | 3-F | Ph | E/Z | CH$_3$ | O | H | CH$_2$—CH$_2$ | Ph | 3,4-(OCH$_3$)$_2$ | log p: 2.44/2.64 |
| 207 | H | 3-Benzothienyl | E/Z | CH$_3$ | O | H | CH$_2$—CH$_2$ | Ph | 3,4-(OCH$_3$)$_2$ | NMR: 3.85(s, 3H) |
| 208 | H | 2-Benzothienyl | E/Z | C$_2$H$_5$ | O | H | CH$_2$—CH$_2$ | Ph | 3,4-(OCH$_3$)$_2$ | log p: 3.24/3.72 |
| 209 | 3-CH$_3$ | Ph | E/Z | CH$_3$ | O | H | CH$_2$—CH$_2$ | Ph | 3,4-(OCH$_3$)$_2$ | log p: 2.56/2.76 |
| 210 | 3-CH$_3$ | Ph | E/Z | C$_2$H$_5$ | O | H | CH$_2$—CH$_2$ | Ph | 3,4-(OCH$_3$)$_2$ | log p: 2.87/31.0 |
| 211 | 3-Br | Ph | E/Z | CH$_3$ | O | H | CH$_2$—CH$_2$ | Ph | 3,4-(OCH$_3$)$_2$ | log p: 2.83/3.05 |
| 212 | 3-Br | Ph | E/Z | C$_2$H$_5$ | O | H | CH$_2$—CH$_2$ | Ph | 3,4-(OCH$_3$)$_2$ | log p: 3.18/3.40 |
| 213 | H | 2-Benzothienyl | E | C$_2$H$_5$ | O | H | CH$_2$—CH$_2$ | Ph | 3,4-(OCH$_3$)$_2$ | NMR: 3.88 (s, 3H) |
| 214 | 3,4-(CH$_2$)$_4$ | Ph | E/Z | CH$_3$ | O | H | CH$_2$—CH$_2$ | Ph | 3,4-(OCH$_3$)$_2$ | log p: 3.17/3.40 |
| 215 | H | 2-Naphthyl | E/Z | C$_2$H$_5$ | O | H | CH$_2$—CH$_2$ | Ph | 3,4-(OCH$_3$)$_2$ | log p: 3.20/3.44 |
| 216 | H | 2-Naphthyl | Z | CH$_3$ | O | H | CH$_2$—CH$_2$ | Ph | 3,4-(OCH$_3$) | log p: 3.10 |
| 217 | H | 2-Naphthyl | E | CH$_3$ | O | H | CH$_2$—CH$_2$ | Ph | 3,4-(OCH$_3$)$_2$ | log p: 2.87 |
| 218 | 4,5-Cl$_2$ | 2-Thiazolyl | E/Z | CH$_3$ | O | H | CH$_2$—CH$_2$ | Ph | 3,4-(OCH$_3$)$_2$ | log p: 2.93/2.95 |
| 219 | 4,5-Cl$_2$ | 2-Thiazolyl | E/Z | C$_2$H$_5$ | O | H | CH$_2$—CH$_2$ | Ph | 3,4-(OCH$_3$)$_2$ | log p: 3.28/3.30 |
| 220 | 4,5-Cl$_2$ | 2-Thiazolyl | Z | CH$_3$ | O | H | CH$_2$—CH$_2$ | Ph | 3,4-(OCH$_3$)$_2$ | log p: 2.93 |
| 221 | 4,5-Cl$_2$ | 2-Thiazolyl | E | CH$_3$ | O | H | CH$_2$—CH$_2$ | Ph | 3,4-(OCH$_3$)$_2$ | Fp.: 74° C. |
| 222 | 4,5-Cl$_2$ | 2-Thiazolyl | E | C$_2$H$_5$ | O | H | CH$_2$—CH$_2$ | Ph | 3,4-(OCH$_3$)$_2$ | log p: 3.28 |
| 223 | 4,5-Cl$_2$ | 2-Thiazolyl | E | C$_2$H$_5$ | O | H | CH$_2$—CH$_2$ | Ph | 3,4-(OCH$_3$)$_2$ | Fp.: 71° C. |

Example A

Phytophthora test (tomato)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and about 20° C.

The evaluation is carried out 6 days after the inoculation.

In this test, compounds 24, 41 and 42 according to the invention show a degree of action of more than 80% at an active compound concentration of 100 ppm in the spray liquor.

Example B

Plasmopara test (vines)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous spore suspension of Plasmopara viticola and then remain in a humidity chamber at 20 to 22° C. and 100% relative atmospheric humidity for 1 day. The plants are then placed in a greenhouse at 21° C. and 90% atmospheric humidity for 5 days. The plants are then moistened and placed in a humidity chamber for 1 day.

Evaluation is carried out 6 days after the inoculation.

In this test, compounds 2, 24, 41, 42, 73, 77, 81, 82, 91, 96, 98, 99, 103, 110, 114, 117, 122, 123, 124, 126, 127, 131, 132, 136, 142, 143, 144, 146, 147, 170, 171 and 173 according to the invention show a degree of action of more than 80% at an active compound concentration of 100 ppm in the spray liquor.

What is claimed is:

1. Compounds of the formula (I)

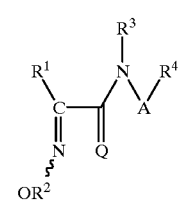

(I)

in which

A represents optionally substituted straight chain alkylene,

Q represents oxygen or sulphur, $R^1$ represents in each case optionally substituted cycloalkyl, cycloalkenyl, or aryl, $R^2$ and $R^3$ are identical or different and in each case represent hydrogen or in each case optionally substituted alkyl, alkenyl, alkinyl or cycloalkyl, and $R^4$ represents in each case optionally substituted cycloalkyl, cycloalkenyl, or aryl.

2. Compounds of the formula (I) according to claim 1, in which

A represents straight chain alkylene having 1 to 6 carbon atoms which is optionally mono- or polysubstituted by identical or different substituents, the preferably substituents preferably being chosen from the following list:

halogen, cyano, nitro, amino, hydroxyl, formyl, carboxyl, carbamoyl or thiocarbamoyl;

in each case straight-chain or branched alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl parts;

cycloalkyl having 3 to 6 carbon atoms;

and substituted aryl optionally mono- or polysubstituted in an identical or different manner by halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or in each case divalent alkylene or dioxyalkylene having in each case 1 to 6 carbon atoms and optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms, Q represents oxygen or sulphur, $R^1$ represents aryl, cycloalkyl or cycloalkenyl having 3 to 7 carbon atoms, in each case optionally mono- or polysubstituted by identical or different substituents, the preferably substituents preferably being chosen from the following list:

halogen, cyano, nitro, amino, hydroxyl, formyl, carboxyl, carbamoyl or thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 8 carbon atoms in the individual alkyl parts;

in each case divalent alkylene or dioxyalkylene having in each case 1 to 6 carbon atoms and in each case optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and substituted aryl, aryloxy, arylthio, arylalkyl, arylalkyloxy, or arylalkylthio, in each case optionally mono- or polysubstituted in an identical or different manner by halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or in each case divalent alkylene or dioxyalkylene having in each case 1 to 6 carbon atoms and optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydrogen, or represents alkyl having 1 to 4 carbon atoms, alkenyl or alkinyl having in each case 2 to 4 carbon atoms or cycloalkyl having 3 to 6 carbon atoms, in each case optionally monoor polysubstituted in an identical or different manner by halogen, cyano, hydroxyl, amino, $C_1$–$C_4$-alkoxy, $C_1$–$C_4$-alkylthio, $C_1$–$C_4$-alkylsulphinyl or $C_1$–$C_4$-alkylsulphonyl (which can in each case be optionally substituted by halogen) or by optionally substituted phenyl, $R^3$ represents hydrogen or alkyl having 1 to 4 carbon atoms, $R^4$ represents aryl, cycloalkyl or cycloalkenyl having 3 to 8 carbon atoms, in each case optionally mono- or polysubstituted by identical or different substituents, the preferably substituents preferably being chosen from the following list:

halogen, cyano, nitro, amino, hydroxyl, formyl, carboxyl, carbamoyl or thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 13 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl parts;

in each case divalent alkylene or dioxyalkylene having in each case 1 to 6 carbon atoms and in each case optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and substituted aryl, aryloxy, arylthio, arylalkyl, arylalkyloxy, or arylalkylthio, in each case optionally mono- or polysubstituted in an identical or different manner by halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or in each case divalent alkylene or dioxyalkylene having in each case 1 to 6 carbon atoms and optionally mono- or polysubstituted in an identical or different manner by halogen and/or straight-chain or branched alkyl having 1 to 4 carbon atoms and/or straight-chain or branched halogenoalkyl having 1 to 4 carbon atoms and 1 to 9 identical or different halogen atoms.

3. Compounds of the formula (I) according to claim 1, in which

A represents methylene, 1,2-ethylene, 1,3-propylene, or 1,4-butylene, which are optionally mono- or polysubstituted in an identical or different manner by fluorine, chlorine, cyano or methoxy, Q represents oxygen or sulphur, $R^1$ represents cyclopropyl, cyclobutyl, cyclopentyl or cyclohexyl, phenyl, or naphthyl, in each case optionally mono- to trisubstituted, the preferably substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl;

cyclopropyl, cyclobutyl, cyclopentyl or cyclohexyl;

phenyl, benzyl, phenoxy and benzyloxy which are optionally substituted by the abovementioned substituents, $R^2$ represents hydrogen, or represents methyl, ethyl, n- or i-propyl or n-, i-, s- or t-butyl, or represents benzyl or propargyl or allyl, $R^3$ represents hydrogen, or represents methyl or ethyl, $R^4$ represents cyclopropyl, cyclobutyl, cyclopentyl or cyclohexyl, phenyl, or naphthyl, in each case optionally mono- to trisubstituted, the preferably substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl;

cyclopropyl, cyclobutyl, cyclopentyl or cyclohexyl.

4. Compounds of the formula (I) according to claim 1, in which

A represents methylene, 1,2-ethylene, 1,1-, 1,2-, 1,3- or 2,2-propylene, 1,1-, 1,2-, 1,3-, 1,4-, 2,2-,2,3-butylene or 1,1-, 1,2- or 1,3-(2-methylpropylene), which are optionally mono- or polysubstituted in an identical or different manner by fluorine, chlorine, cyano or methoxy, Q represents oxygen or sulphur, $R^1$ represents cyclobutyl, cyclopentyl or cyclohexyl, in each case optionally mono- to hexasubstituted, the substituents being those mentioned below;

or represents phenyl, or naphthyl, in each case optionally mono- to trisubstituted, the preferably substituents being chosen from the following list:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl;

cyclopropyl, cyclopentyl or cyclohexyl;

phenyl, phenoxy or benzyloxy optionally substituted by the abovementioned substituents;

$R^2$ represents hydrogen, methyl, ethyl, n- or i-propyl or n-, i-, s- or t-butyl, or represents benzyl or allyl, $R^3$ represents hydrogen or methyl, $R^4$ represents cyclopropyl, cyclobutyl, cyclopentyl or cyclohexyl, in each case optionally mono- to hexasubstituted, the substituents being those mentioned below;

or represent phenyl, or naphthyl, in each case optionally monoto trisubstituted, the preferably substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl, cyclopropyl, cyclobutyl, cyclopentyl or cyclohexyl.

5. Compounds of the formula (I) in which

A represents methylene, 1,2-ethylene, or 1,3-propylene,

Q represents oxygen, $R^1$ represents phenyl, which is optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio, or represents phenyl which is substituted by in each case optionally fluorine-substituted 3,4-methylene- and ethylenedioxo, propane-1,3-diyl and butane-1,4-diyl, or represents naphthyl, $R^2$ represents hydrogen, methyl or ethyl, or represents n- or i-propyl, or represents n-, i-, s- or t-butyl, or represents benzyl or allyl, $R^3$ represents hydrogen or methyl, $R^4$ represents cyclohexyl or optionally mono- to trisubstituted phenyl, the preferably substituents preferably being chosen from the following list:

fluorine, chlorine, bromine, cyano, nitro, amino, hydroxyl, formyl, carboxyl, carbamoyl, thiocarbamoyl, methyl, ethyl, n- or i-propyl, n-, 1-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case divalent trimethylene (propane-1,3-diyl), tetramethylene (butane-1,4-diyl), methylenedioxy or ethylenedioxy, in each case optionally mono- or polysubstituted in an identical or different manner by fluorine, chlorine, methyl, trifluoromethyl, ethyl or n- or i-propyl.

6. Process for the preparation of compounds of the formula

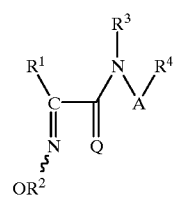

(I)

in which

A, Q, $R^1$, $R^2$, $R^3$ and $R^4$ have the meaning disclosed in claim 1, characterized in that carboxylic acid derivatives of the general formula (II)

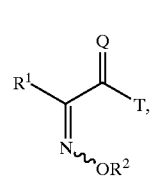

(II)

in which $R^1$, $R^2$ and Q have the abovementioned meaning and

T represents hydroxyl, halogen or alkoxy, are reacted with an amine of the general formula (III)

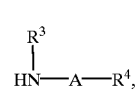

(III)

in which $R^3$, $R^4$ and A have the abovementioned meaning or with a hydrogen halide thereof optionally in the presence of an acid acceptor, optionally in the presence of a condensing agent and optionally in the presence of a diluent.

7. A composition for combating pests comprising a pesticidally effective amount of a compound of the formula (I) according to claim 1 and an extender and/or a surface active agent.

8. A method of combating pests comprising applying a pesticidally effective amount of a compound of the formula (I) according to claim 1 to the pests or their environment or to a place from which it is desired to exclude such pests.

* * * * *